United States Patent [19]
Sawan et al.

[11] Patent Number: 5,490,938
[45] Date of Patent: Feb. 13, 1996

[54] LIQUID DISPENSER FOR STERILE SOLUTIONS

[75] Inventors: Samuel P. Sawan, Tyngsboro, Mass.; Tadmor Shalon, Brentwood, Mo.; Sundar Subramanyam, Stoneham; Alexander Yurkovetskiy, Acton, both of Mass.

[73] Assignee: BioPolymerix, Inc., Tyngsboro, Mass.

[21] Appl. No.: 170,510

[22] Filed: Dec. 20, 1993

[51] Int. Cl.$^6$ .......................... B01D 61/00; B67D 5/58; A61B 19/00
[52] U.S. Cl. .................... 210/651; 210/650; 210/490; 210/506; 210/473; 210/474; 210/321.84; 222/420; 604/406
[58] Field of Search .................. 210/490, 506, 210/650, 651, 653, 500.23, 346, 473, 474, 321.84, 500.25; 222/189, 420; 604/405, 406

[56] References Cited

U.S. PATENT DOCUMENTS

| | | | |
|---|---|---|---|
| 4,150,171 | 4/1979 | Feldstein | 427/261 |
| 4,304,894 | 12/1981 | Andrews et al. | 526/310 |
| 4,463,880 | 8/1984 | Kramer et al. | 222/189 |
| 4,494,663 | 1/1985 | Bertaud et al. | 215/232 |
| 4,533,068 | 8/1985 | Meierhoefer | 222/189 |
| 4,882,232 | 11/1989 | Bugnet et al. | 204/192.14 |
| 4,917,271 | 4/1990 | Kanner et al. | 222/189 |
| 4,938,389 | 7/1990 | Rossi et al. | 222/189 |
| 5,025,957 | 6/1991 | Ranalletta et al. | 222/189 |
| 5,040,706 | 8/1991 | Davis et al. | 222/541 |
| 5,049,139 | 9/1991 | Gilchrist | 604/265 |
| 5,060,823 | 10/1991 | Perlman | 222/1 |
| 5,074,440 | 12/1991 | Clements et al. | 222/189 |
| 5,105,993 | 4/1992 | LaHaye et al. | 222/189 |
| 5,110,470 | 5/1992 | Yokosawa et al. | 210/500.25 |
| 5,265,770 | 11/1993 | Matkovich et al. | 210/321.84 |

FOREIGN PATENT DOCUMENTS

| | | |
|---|---|---|
| 4-70935 | 1/1986 | Japan . |
| 61-8104 | 1/1986 | Japan . |
| 2-68105 | 3/1990 | Japan . |
| 2-192937 | 7/1990 | Japan . |
| 4-197363 | 7/1992 | Japan . |
| 4-197362 | 7/1992 | Japan . |
| 2254340 | 7/1992 | United Kingdom . |

OTHER PUBLICATIONS

Liedberg, H. et al., "Assessment of silver-coated urinary catheter toxicity by cell culture", Urol. Res., 17:359–360, 1989.
Williams, R. et al., "The Biocompatibility of Silver", CRC Crit. Rev. Biocompat., vol. 5, Issue 3, pp. 221–243, 1989.
Boarini, E. et al., "Case Study: Development Of A Device With An Antimicrobial Treatment", Medical Plastics Today and Tomorrow Proc. Med. Plast. Conf., Publ. Soc. Plastics Engineers, Brookfield, CT., 1990.
Leung, J. W. C. et al., "Decreased bacterial adherence to silver-coated stent material: an in vitro study", Gastorintestinal Endoscopy, vol. 38, No. 3, pp. 338–340, 1992.
Erck, R. A. et al., "Adhesion of Silver Films to Ion-Bombarded Zirconia", Lubrication Engineering, vol. 47, 8, pp. 640–644, Aug., 1991.
Erdemir, A. et al., "Ion-Assisted Deposition of Silver Films on Ceramics for Friction and Wear Control", J. Soc. Tribologists and Lubrication Engineers, pp. 23–30, Jan., 1990.

(List continued on next page.)

Primary Examiner—Ana M. Fortuna
Attorney, Agent, or Firm—Testa, Hurwitz & Thibeault

[57] ABSTRACT

A liquid dispenser for dispensing sterile liquid comprising a container for storing the sterile liquid, a nozzle assembly mounted on the container, and a filter which has at least one surface and a plurality of its pores coated with a metallic material, e.g., a metal or metal oxide or metal salt, that is bacteriostatic or bacteriocidal, is described. The metal coated filter, methods for coating the filter, and methods for using the liquid dispenser are also provided.

18 Claims, 2 Drawing Sheets

OTHER PUBLICATIONS

Mastrototaro, J. et al., "Rigid and Flexible Thin–Film Multi–electrode Arrays for Transmural Cardiac Recording", IEEE Transactions On Biomedical Engineering, vol. 39, No. 3, pp. 271–279, Mar., 1992.

Pyle, B. H. et al., "Efficacy of copper and silver ions with iodine in the inactivation of *Pseudomonas cepacia*", Jrnl. of Applied Bacteriology, 72:71–79, 1992.

Davis, C. P. et al., "Electrode And Bacterial Survival With Ion–tophoresis In Synthetic Urine", The Jrnl. of Urology, vol. 147, pp. 1310–1313, May 1992.

Zanoni, D. et al., "A Comparison of Silver Nitrate with Erythromycin for Prophylaxis Against Ophthalmia Neonatorum", Clinical Pediatrics, pp. 295–298, May 1992.

Farrah, S. R. et al., "The production of antibacterial tubing, sutures and bandages by in situ precipitation of metallic salts", Can. J. Microbiol., vol. 37, pp. 445–449, 1991.

Chu, C. C. et al., "Newly made antibacterial braided nylon sutures. I. In vitro qualitative and in vivo preliminary bio–compatibility study", Jrnl. of Biomedical Materials Res., vol. 21, pp. 1281–1300, 1987.

Clark, R. E. et al., "Antibacterial Vascular Grafts With Improved Thromboresistance", Arch. Surg., vol. 109, pp. 159–162, Aug., 1974.

Tsai, W. C. et al., "In Vitro quantitative Study Of Newly Made Antibacterial Braided Nylon Sutures", Surgery, Gynecology & Obstetrics, vol. 165, pp. 207–211, Sep., 1987.

Smoot, E. C., et al., "In Vitro Toxicity Testing for Anti–bacterials Against Human Keratinocytes", Plastic and Reconstructive Surgery, vol. 87, No. 5, pp. 917–924, May, 1991.

Liedberg, H. et al., "Silver coating of urinary catheters prevents adherence and growth of *Pseudomonas aeruginosa*", Urol. Res., 17:357–358, 1989.

Gravens, D. L. et al., "The antibacterial effect of treating sutures with silver", Surgery, vol. 73, No. 1, pp. 122–127, Jan., 1973.

Herruzo–Cabrera, R., "Evaluation of the penetration strength, bactericidal efficacy and spectrum of action of several antimicrobial creams against isolated microorganisms in a burn centre", Burns, vol. 18, No. 1, pp. 39–44, 1992.

Laibinis, P. E., et al., "Comparison of the Structures and Wetting Properties of Self–Assembled Monolayers of n–Alkanethiols on the Coinage Metal Surfaces, Cu, Ag, Au" J. Am. Chem. Soc., 113, pp. 7152–7167, 1991.

Bain, C. D. et al., "Formation of Monolayer Films by the Spontaneous Assembly of Organic Thiols from Solution onto Gold", J. Am. Chem. Soc., 111, pp. 321–335, 1989.

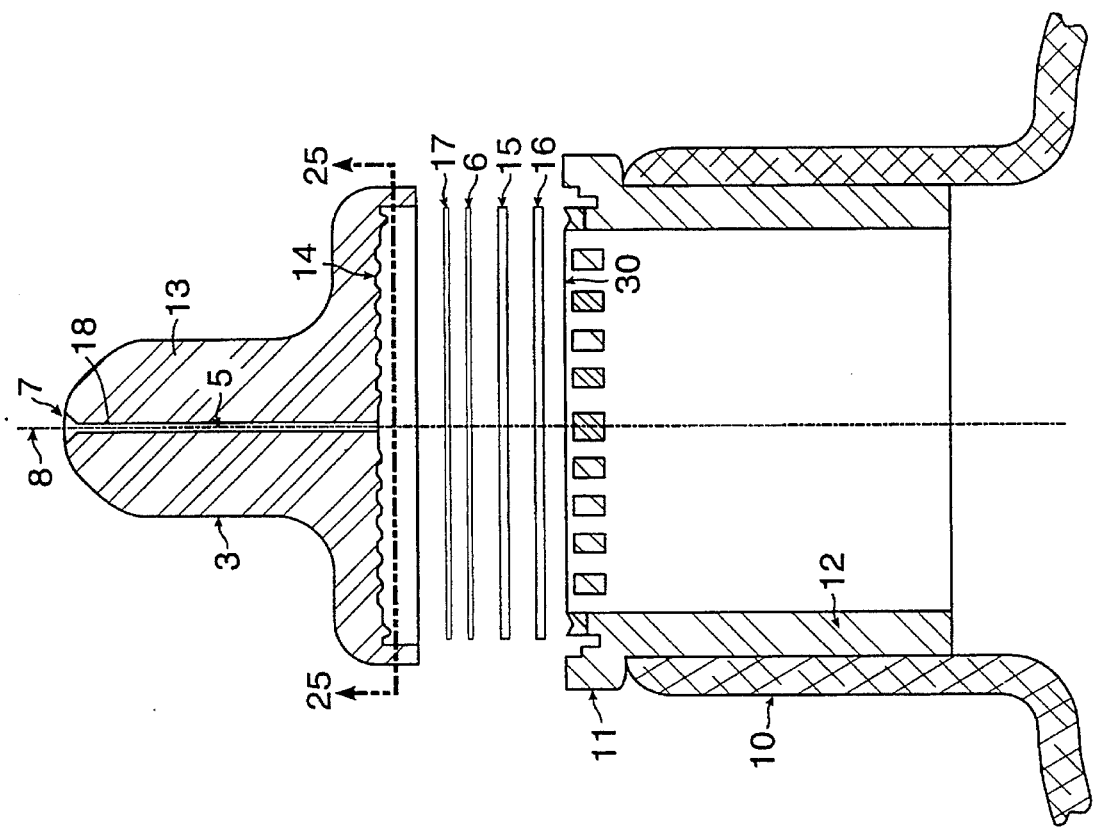
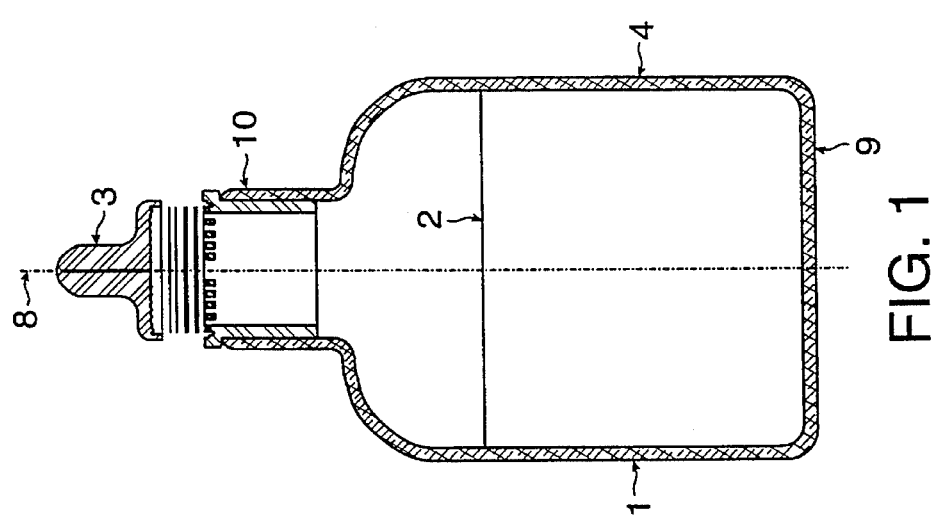

LIQUID DISPENSER FOR STERILE SOLUTIONS

FIELD OF THE INVENTION

The present invention relates to liquid dispensers, specifically, the provision of liquid dispensers capable of maintaining sterile solutions during storage, during dispensing, and subsequent to dispensing of the solution, as well as methods of manufacture and use of such dispensers.

BACKGROUND OF THE INVENTION

Administration of sterile solutions is required for many prescription and non-prescription materials. In general, such solutions, and the dispensers in which they are stored, are sterilized prior to closure of the dispenser. Contamination can occur, however, after the dispenser is opened and used. Various approaches have been employed in attempts to decrease this contamination problem.

Single dose dispensers are available. Such dispensers, however, are made only for one time use, and are then discarded, adding considerably to packaging costs. Moreover, more sterile solution than is required for a single dose is usually packaged which also adds to the expense of the treatment. Another problem is that persons may attempt to use the single dose dispenser multiple times, which can result in contaminated liquid being dispensed.

Alternatively, preservatives have been added to multi-dose dispensers to prevent microbial contamination after the dispenser is initially used. Such preservatives, however, are often toxic to mammalian cells, as well as microbial cells. For example, many preservatives used in eye drop formulations are toxic to the goblet cells in the eye. Such toxicity is detrimental to persons requiring prolonged application of the solutions. Moreover, persons often develop chemical sensitivity to the preservative, resulting in significant allergic reactions to the preparations. Such allergies can appear in some persons after prolonged exposure, as well as in others after only a single exposure.

Membrane filters have also been used in liquid dispensers in attempts to prevent microbial contamination of the stored sterile liquid. If a hydrophilic filter is used, however, the filter can allow the phenomenon known as "grow-through," in which microbial progeny on the downstream (non-sterile) side of the filter can pass through the filter pores because of their smaller size during cell division, and thereby contaminate the sterile solution contents in the dispenser.

Hydrophobic filters have also been employed in liquid dispensers. Hydrophobic surfaces are non-wetting, and therefore are significantly more difficult for microbes to grow on. Such filters, however, because of their hydrophobicity will not allow the flow of sterile aqueous solutions through the filter.

SUMMARY OF THE INVENTION

It is an object of the invention to provide a multi-dose sterile liquid dispenser.

It is another object of the invention to provide a liquid dispenser that maintains the sterility of the liquid within the liquid dispenser during storage, during dispensing of the liquid, and subsequent to dispensing of the liquid.

It is yet another object of the invention to provide a multi-dose liquid dispenser that does not require the use of a preservative to maintain sterility of the liquid, thereby reducing toxicity and allergy problems.

It is yet another object of the invention to provide a membrane filter in a liquid dispenser that has been coated with a metal that is bacteriostatic or bacteriocidal in order to reduce microbial growth and "grow-through" on the filter.

It is yet another object of the invention to provide a filter in a liquid dispenser that has been coated with a metal that renders the filter hydrophilic so as to allow a reasonable flow rate of the sterile liquid through the filter at a low pressure.

It is yet another object of the invention to provide a filter that has been coated on at least one surface and within the pores, with a metal, e.g., silver, for use in maintaining the sterility of the liquid contents of liquid dispensers.

It is yet another object of the invention to provide a filter that has been coated on at least one surface with a bacteriostatic or bacteriocidal agent that is covalently attached to a metallic coating, for use in maintaining the sterility of the liquid contents of liquid dispensers.

It is yet another object of the invention to provide a coating of silver in the passageway of the nozzle of a liquid dispenser with a filter, to reduce microbial growth in any residual liquid that forms on the downstream side of the filter after dispensing the liquid through the filter and nozzle.

It is yet another object of the invention to provide a liquid dispenser that can be used for dispensing preservative-free eyecare products such as liquid artificial tears, solutions for contact lens care and medicaments.

It is yet another object of the invention to provide a liquid dispenser that can be used for dispensing preservative-free liquid medicaments that are required to be sterile to any part of the body or onto an object that is to be placed into the body.

It is yet another object of the invention to provide a method for electroless deposition of a metal, e.g., silver, onto a filter so that the surface and pores of the filter are coated with a substantially uniform layer of the metal.

Still another object of the invention is to provide a liquid dispenser for sterile liquids which is economical, efficient and durable.

According to the invention, a liquid dispenser, e.g., a multi-dose dispenser, for dispensing a sterile liquid is provided. The liquid dispenser has a container for storing the sterile liquid and a nozzle assembly which is mounted on the container. The nozzle assembly has a passageway which enables the sterile liquid to flow from the container through the passageway when the liquid is dispensed. The liquid dispenser also has a filter which is attached to the nozzle assembly so that the filter extends across the passageway to direct liquid and air flow through the filter from the container to the downstream surface of the filter.

The filter, e.g., an organic filter or inorganic filter, is at least partially coated on the downstream surface with a metallic material, e.g., a metal such as silver, or a metal oxide, or a metal salt, or mixtures thereof, that is bacteriostatic or bacteriocidal. The filter has pores of a size, e.g., approximately 0.1 microns to approximately 1.2 microns, preferably, approximately 0.22 microns to approximately 0.65 microns, which preclude passage of microorganisms through the filter, and permit passage of the sterile liquid from the container through the filter.

The filter is also at least partially coated within a plurality of its pores with the metallic material. Variations include the upstream surface of the filter also being at least partially coated with the metallic material.

Other variations are the surfaces and plurality of pores of the filter being at least partially coated with an additional different metallic material that is bacteriostatic or bacteriocidal. A variation is the liquid dispenser having a second filter that is serially aligned with the first metal coated filter, and which is at least partially coated on at least one surface and within a plurality of its pores with a different metallic material that is bacteriostatic or bacteriocidal.

In certain embodiments, the filter and a plurality of the pores which are coated with one or more metallic materials can have at least a partial additional coating with a compound that has an anti-viral or anti-bacterial property.

In another embodiment, the filter includes a hydrophobic portion for allowing air to enter the container to replace the sterile liquid that is dispensed from the filter dispenser.

In yet another embodiment of the invention, the passageway walls in the nozzle assembly, at least on the downstream side of the filter, are coated with a metallic material that is bacteriostatic or bacteriocidal.

In other variants, the liquid dispenser can have a prefilter which is spaced upstream from the filter for providing a barrier to the passage of particulate matter through the prefilter and for permitting the passage of sterile liquid from the container through the prefilter. A support means can also be spaced upstream from the filter for reinforcement of the filter.

Another aspect of the invention is a dispenser for dispensing sterile liquids which has a filter attached to a container for liquids, the improvement being the filter being at least partially coated on the downstream surface with a metallic material that is bacteriostatic or bacteriocidal; the filter extending across a passageway provided by the container leading from the container to a dispensing area where the liquid is dispensed; the filter having pores with a pore size so as to preclude passage of microorganisms therethrough and so as to permit passage of sterile liquid from the container therethrough; and the filter also being at least partially coated within a plurality of the pores with the metallic material.

Yet another aspect of the invention features a filter having pores providing liquid conduits interconnecting the upstream and downstream surfaces of the filter for liquid passage from one of the surfaces to the other. The pores are of a size so as to preclude passage of microorganisms through the filter and so as to permit passage of liquid and air through the filter. At least one surface of the filter is at least partially coated with a metallic material, e.g., a metal such as silver, or a metal oxide, or a metal salt, or mixtures thereof, that is bacteriostatic or bacteriocidal, and the filter further is at least partially coated within a plurality of the pores with the metallic material. Variations include the upstream surface also being at least partially coated with the metallic material. Also, the filter surfaces and a plurality of the pores can be at least partially coated with an additional metallic material that is bacteriostatic or bacteriocidal, and/or a different compound that has an anti-viral or anti-bacterial property.

The invention also includes a method in which a sterile liquid can be dispensed by applying pressure to the container of the liquid dispenser of this invention so as to discharge the sterile liquid from the container. The container preferably is formed at least in part of a resiliently deformable material, such as an elastic polymer, which permits manual squeezing, e.g., to discharge a dose of medicament, and subsequent elastic recovery of the material to its original configuration by drawing gas from a surrounding atmosphere into the container while the gas is sterilized by the filter in passing therethrough.

In one embodiment of the invention, the liquid dispenser is used for eyecare in an organism, in which a sterile eyecare liquid, e.g., liquid artificial tears, a solution for contact lens care or a medicament, is dispensed from the liquid dispenser into the eye or onto an object that is to be placed into the eye. Preferably, the eyecare liquid is preservative-free.

The invention also features a method for coating the surface and pores of a filter with a metal by providing a filter with pores, contacting the filter with a carbonyl compound, e.g., an aldehyde such as glutaraldehyde, a sugar such as glucose, or an aldehyde functionality generating compound, drying the filter, contacting the dried filter with a metal salt, e.g., silver nitrate, or metal carboxylate salt solution, e.g., silver tartrate, and an amine-containing compound solution, e.g., ammonium hydroxide, so as to deposit the metal on the surface and within a plurality of the pores of the filter. In an alternative embodiment, the filter drying step is omitted.

In another embodiment, a filter having pores is provided, the filter is contacted with an activator, e.g., tin dichloride, the filter is dried, and the filter is contacted with a metal salt or metal carboxylate salt solution, either with or without an amine-containing compound solution, so as to deposit the metal on the surface and within a plurality of the pores of the filter.

Products made in accordance with these methods are also included in this invention.

The above and other objects, features and advantages of the present invention will be better understood from the following specification when read in conjunction with the accompanying drawings.

BRIEF DESCRIPTION OF THE DRAWINGS

FIG. 1 is a semi-diagrammatic cross-sectional view of a liquid dispenser in accordance with the present invention.

FIG. 2 is a semi-diagrammatic cross-sectional view of an upper portion of the liquid dispenser of FIG. 1.

DETAILED DESCRIPTION

Figure 3:
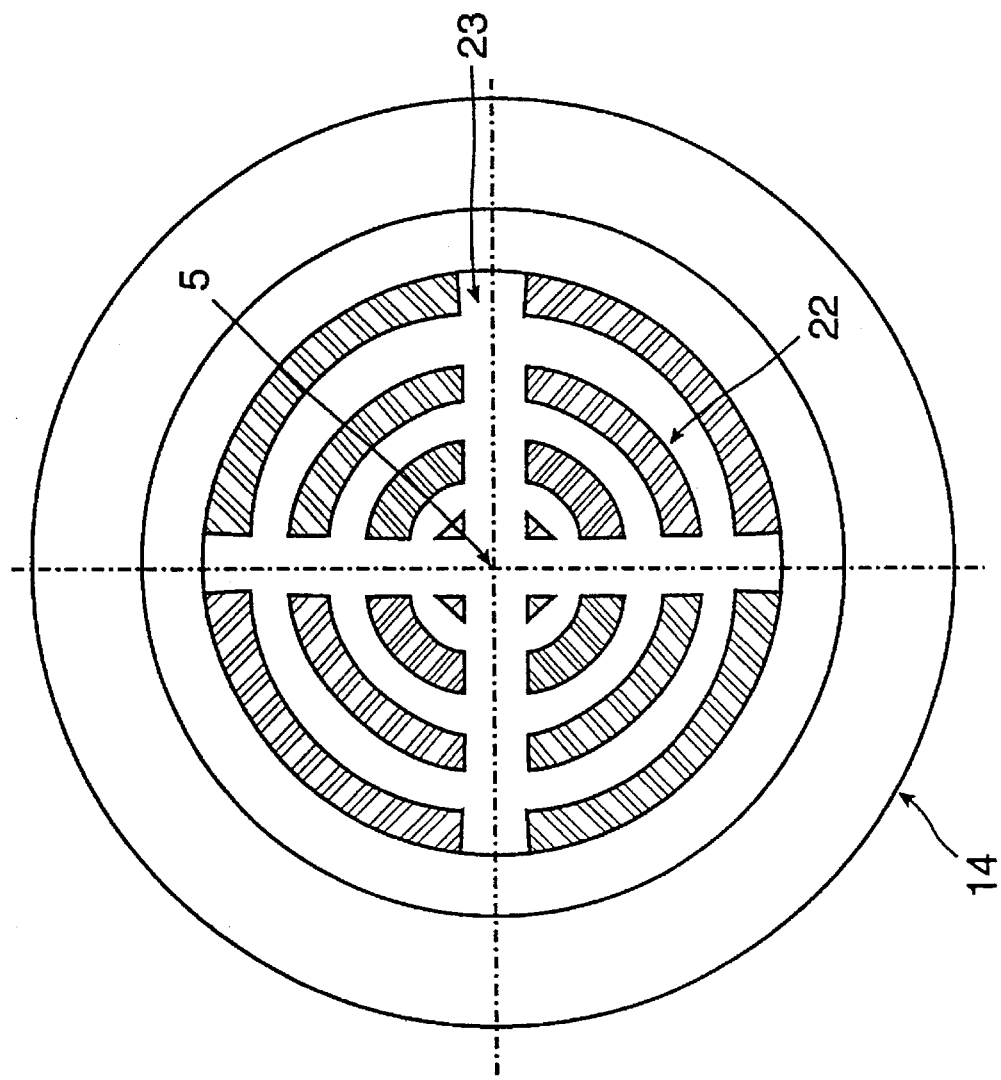
FIG. 3 is a semi-diagrammatic top view taken through line 25—25 of FIG. 2 showing the concentric and radial channels of the invention.

This invention, as shown in FIGS. 1–3, provides a liquid dispenser 1 for dispensing a sterile liquid 2. The liquid dispenser 1 has a container 4 for storing sterile liquid 2 and a nozzle assembly 3 which is mounted on top of container 4. Nozzle assembly 3 has a passageway 5 which enables sterile liquid 2 to flow from container 4 through passageway 5 when sterile liquid 2 is dispensed.

Container 4 is designed to permit manual squeezing so as to force sterile liquid 2 from container 4 through filter 6 out of orifice 7 of nozzle assembly 3. In normal operation, liquid dispenser 1 is inverted and container 4 is squeezed.

Container 4, as shown in FIG. 1, has a circular cross-section extending along a vertical axis 8, with a flat bottom 9 and an upper end 10. Sidewall thickness is preferably in the range of 0.01 to 0.25 inch. However, various sizes and configurations can be used. The shape of the container can be round, elliptical, polygonal, irregular, or the like, and in some cases may be in tube form. The particular sidewall thickness can vary greatly, as can the volume of the chamber within container 4 that holds the medicament or other liquid to be dispensed. Thus, various sizes ranging from cubic millimeters to cubic centimeters or more can be used for the container chamber.

In the preferred embodiment, the nozzle assembly 3 is an ovoid form. The nozzle assembly has a cross-section formed of a plastic material which is self-supporting and defines a generally ovoid configuration having an inverted lip portion 11 mating with and sealed to the top of container 4 at upper end 10. Nozzle assembly 3 includes within it a ring-shaped lower spacer 12 of a solid material having a central passage connecting the chamber of container 4 with the filter or filters and an upper spacer 13 which acts to hold the filter or filters in place. The lower spacer 12 comprises a supporting screen 30. A disc 14 carries channel means. As shown in FIG. 3, disc 14 carries a plurality of concentric channels 22 which are interconnected by radial channels 23 to a central passageway 5 so that liquid coming from container 4 will pass through the filter or filters and be distributed on the surface of disc 14 so as to cause dispensed sterile liquid 2 to coalesce into a single drop or a stream of liquid when expelled from container 4. Depending on factors including, e.g., the applied pressure, the viscosity of the expelled liquid and the surface area of disc 14, either a single drop or a stream of liquid will be dispensed. Disc 14 is held in place by being adhesively secured, e.g., by ultrasonic welding or by a mechanical force, to the upper spacer 13. Support 16, prefilter 15, filter 6 and second filter 17 can be suspended by spacers 12 and 13. In some embodiments, only filter 6 need be used and one or more of the support, prefilter or second filter, can be eliminated. Various combinations of these elements can be used in different embodiments as desired.

While the prefilter and filter, as well as the second filter, are shown as planar members, various configurations can be used. These members can be in the form of cones, polygonal or other shaped devices as may be desirable for specific applications. Planar sheet-type materials as shown are preferred.

While passageway 5 is preferably axially extending with a circular cross-section, it can have any configuration as desired for specific applications.

Container 4 can be formed, e.g., from a flexible material, e.g., an elastically deformable polymer, e.g., thermosetting or thermoplastic polymeric material, e.g., polypropylene, polyethylene, polyvinylchloride, polyethylene terephthalate, polytetrafluoroethylene, polysulfone and polyethersulfone. In some cases the container can be a deformable metallic or plastic medicament container, such as a toothpaste tube, where the container may remain deformed after each dose is dispensed.

Nozzle assembly 3 can be formed from the same or a more rigid type of material than container 4. In one embodiment, nozzle assembly 3 is permanently attached to container 4 with a liquid-tight connection so as to aid in maintaining sterility of sterile liquid 2 in container 4. Such a connection can be formed by standard techniques, e.g., ultrasonic welding, heat press sealing, adhesive sealing or mechanical sealing.

Filter 6 is sealingly attached to nozzle assembly 3 so that filter 6 extends across the entire expanse of passageway 5 to direct liquid and air flow out of and into container 4 through filter 6. Filter 6 can be attached to nozzle assembly 3 by any method which results in such a seal, including, e.g., ultrasonic sealing, heat press sealing and adhesive sealing.

By filter is meant any material which can function as a microbial filter, e.g., membranes. The filter of this invention includes, e.g., organic and inorganic filters. Organic filters include, e.g., any polymeric material which can be used for the preparation of membranes or filter papers. Examples of organic filters include polysulfone, polyethersulfone, polyamide, e.g., nylon, polycarbonate, polyacrylate, polyvinylidene fluoride, polyethylene, polypropylene, cellulosics, e.g., cellulose, and Teflon®. Any of the hydrophobic materials, e.g., polypropylene or Teflon®, require prior activation with techniques such as plasma, chemical oxidation or metallic sensitization, e.g., a primer. Inorganic filters include, e.g., glass fiber filter paper, ceramic membranes, e.g., alumina or silica, and metal filters. Sintered glass and sintered ceramic blocks can also be used. The filters can be either hydrophilic or hydrophobic. If a hydrophobic filter is used, the metal coating, described below, converts it to a filter with hydrophilic properties.

Filter 6 has pores which form interconnecting liquid conduits extending from an upstream surface of the filter to a downstream surface. The pore size for filter 6 is chosen so that the pores permit passage of sterile liquid 2 from container 4 through filter 6, but preclude passage of microorganisms through filter 6, thereby maintaining the sterility of sterile liquid 2 in container 4. By microorganism is meant bacteria, blue-green algae, fungi, protozoa and algae. The pore size can range, e.g., from approximately 0.1 microns to approximately 1.2 microns. Preferably, the pore size is approximately 0.22 microns to approximately 0.65 microns. Most preferably, the pore size is 0.65 microns. Whereas 0.22 microns is the pore size used in most bacterial filtration systems, this invention can produce a sterile filtrate with larger pore sizes, e.g., 0.45 and 0.65 microns, thus permitting a device which gives a faster flow rate for the dispensed liquid.

A major problem in multi-dose liquid dispensers is that liquid may accumulate downstream of the filter subsequent to dispensing liquid from the container. By downstream of the filter is meant that it is on the side of the filter that liquid from the container which has passed through the filter would be on, e.g., the surface of the filter exposed to the outside atmosphere. By upstream of the filter is meant that it is on the side of the filter that liquid from the container which has not yet passed through the filter would be on. Microorganisms can multiply in this accumulated downstream liquid which can contaminate subsequent drops which are dispensed and which come into contact with the accumulated liquid on the downstream side of the filter. Moreover, certain microorganisms in this accumulated liquid can, because of their smaller size during cell division, pass through the pores of the filter, a phenomenon known as "grow-through," and contaminate the sterile liquid upstream of the filter.

This invention addresses this problem by having filter 6 be at least partially coated on the downstream surface and within a plurality of the pores with a metallic material, e.g., a metal or metal oxide or metal salt or mixtures thereof, that is bacteriostatic or bacteriocidal. By bacteriocidal is meant the killing of microorganisms. By bacteriostatic is meant inhibiting the growth of microorganisms which can be reversible under certain conditions. By a metallic material that is bacteriostatic or bacteriocidal is meant a metallic material that is bacteriostatic to a microorganism, or that is bacteriocidal to a microorganism, or that is bacteriocidal to certain microorganisms and bacteriostatic to other microorganisms. In certain embodiments, filter 6 is also at least partially coated on the upstream surface with a metallic material, e.g., a metal or metal oxide or metal salt or mixtures thereof. Any metal which is bacteriostatic or bacteriocidal can be used. Examples of such metals include, e.g., silver, zinc, cadmium, mercury, antimony, gold, aluminum, copper, platinum and palladium. The appropriate metal coating is chosen based upon the use to which the sterile liquid passing over the metal coated filter is to be put. Preferably, metals which are not toxic are coated on filters which are to be used for filtering solutions that are to be applied to humans and other organisms. The preferred metal is silver.

In one embodiment, filter 6 has both hydrophilic and hydrophobic regions. For example, a hydrophobic filter which has only been coated with a metal or metal oxide or metal salt on a portion of the filter, will be hydrophilic for the coated portion and hydrophobic for the uncoated portion. In another example, a hydrophilic or hydrophobic filter is coated with a metal, metal oxide or metal salt, so as to make the filter hydrophilic, and then a portion of this metallic surface is rendered hydrophobic by the incorporation of a hydrophobic coating, e.g., an alkyl mercaptan such as octyl mercaptan. Such a dual purpose filter is preferred when multiple doses of liquid are dispensed in quick succession to each other, in order to more quickly replace the liquid which has been dispensed from the container with air from outside the container, so as to equalize the pressure. The dispensed liquid can pass through the hydrophilic portion of the filter, and the replacement air can pass through the hydrophobic portion without being hampered by the presence of liquid on the hydrophilic portion.

In the embodiment of FIG. 2, an air port or vent (not shown) can be provided through upper spacer 13 so as to allow air passage to container 4 as the liquid is dispensed from container 4. The air port or vent provides for compensation of the air pressure as liquid is dispensed from the container so as to avoid formation of a vacuum. The device will work with or without the air port or vent, however, if a constant and sustained flow is desired, better flow rates may be obtained with the use of an air port or vent. In those cases where a hydrophobic/hydrophilic membrane is used, the air port or vent described may be particularly desirable to equalize pressure as liquids leave the container. In such a case, it is preferred that the air port or vent be positioned above the hydrophobic portion of the filter.

The invention also provides for a filter in which the downstream surface and a plurality of the pores are at least partially coated with an additional second metallic material, e.g., a metal or metal oxide or metal salt or mixtures thereof, that is bacteriostatic or bacteriocidal. In one embodiment, the upstream surface is also at least partially coated with the second metal or metal oxide or metal salt. Examples of metals that can be used are discussed above in relation to the single metal coating. The use of two different metals can enhance the anti-microbial properties of the filter. Different types of microorganisms can exhibit different degrees of sensitivity to different metals. In addition, the use of two different metals can significantly reduce the problem of selection for microorganisms having resistance to the metal in the metal coating that can occur when only one metal is used.

Another variation of the invention is a liquid dispenser which has a second filter 17 with pores of a size that permits passage of sterile liquid 2 from container 4, that is serially aligned with filter 6. Second filter 17 is at least partially coated on at least one surface and within a plurality of its pores with a different metallic material, e.g., a metal or metal oxide or metal salt or mixtures thereof, that is bacteriostatic or bacteriocidal, than is used for the coating on filter 6. The presence of different metals on different filters in the liquid dispenser is advantageous for the same reasons as discussed above regarding the embodiment where two different metals are applied to a single filter. In other embodiments, more than two different metal or metal oxide or metal salt coated filters are present.

In another embodiment of this invention, the downstream surface of the filter and a plurality of pores of the filter, which are coated with one or more metals or metal oxides or metal salts, has at least a partial additional coating with a compound that has an anti-viral or anti-bacterial property. By anti-viral is meant capable of killing, or suppressing the replication of, viruses. By anti-bacterial is meant bacteriostatic or bacteriocidal. Such a compound can be non-metallic. This additional coating can allow for more effective anti-bacterial liquid dispensers, in that different anti-bacterial compounds can exhibit different degrees of effectiveness for different types of microorganisms. Multiple anti-bacterial compounds also significantly reduce the problem of selection for microorganisms having resistance to the metal in the metal coating, as discussed above. Moreover, this additional coating can allow for joint anti-bacterial/anti-viral liquid dispensers. Preferably, this compound is bound as a monolayer to at least a portion of the metal coating on the filter. Any compound which has anti-bacterial or anti-viral activity can be used. Examples of such compounds include, e.g., benzalkoniumchloride thiol, (the synthesis of which is described in Example 9), polycationic compounds, e.g., α-4-[1-tris(2-hydroxyethyl) ammonium-2-butenyl] poly[1-dimethylammonium-2-butenyl]-ω-tris(2-hydroxyethyl) ammonium chloride, and biguanides of the general formula:

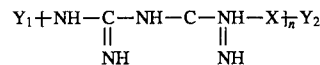

or their water soluble salts, where X is any aliphatic, aromatic, substituted aliphatic or aromatic, or a mixture of any of these, and $Y_1$ and $Y_2$ are any aliphatic, aromatic, substituted aliphatic or aromatic, or a mixture of any of these, and where n is an integer equal to or greater than 1, e.g., chlorhexidine or polyhexamethylene biguanide (available from Zeneca of Wilmington, Del.). These compounds are modified to include a thiol group in their structure so as to allow for the bonding of the compound to the metallic surface of the filter.

Filters with the various coatings described above are also included in this invention.

The invention also includes an embodiment in which the liquid dispenser has a prefilter 15 which is spaced upstream from filter 6 and provides a barrier to the passage of particulate matter through prefilter 15, while permitting passage of sterile liquid 2 from container 4 through prefilter 15. In this manner, particulate matter that may be present in sterile liquid 2 in container 4 does not need to be filtered by filter 6, and thus prevents clogging of filter 6, thereby aiding in preserving the capacity of, and flow rate through, filter 6. Preferably, the pore size of prefilter 15 is approximately 1 micron to approximately 50 microns. The prefilter material includes, e.g., glass fibers, synthetic polymer fibers, e.g., hydrophilic polypropylene fibers, nylon and cellulosic fibers. Preferably, prefilter 15 is attached to filter 6 in embodiments where there is only one filter, or attached to the most upstream filter where there is more than one filter, and is also attached to nozzle assembly 3. Preferably, the attachments are by welding.

In another embodiment, the liquid dispenser has a support 16 which is spaced upstream from the filter to act as a reinforcement for the filter. Preferably, support 16 is perforated. Support 16 can be made from any material that the container or nozzle assembly is made from.

In other embodiments of the invention, the internal walls 18 of nozzle assembly 3 are at least partially coated with a metallic material, e.g., a metal or metal oxide or metal salt or mixtures thereof, that is bacteriostatic or bacteriocidal. After the liquid dispenser of the invention has initially been used to dispense liquid from container 4, some residual liquid may remain on internal walls 18 of nozzle assembly 3 downstream from filter 6. Microorganisms can grow in this residual liquid and contaminate any future drops of liquid which are dispensed. By coating these walls with an antibacterial metallic material, this contamination is reduced. Examples of metals which can be used to coat the nozzle assembly walls were discussed above in relation to coating filter 6. Example 10 describes a method for depositing silver onto the walls of the nozzle assembly.

In methods of the invention a surface and pores of a filter are coated with a metal. In one embodiment, a filter having pores is provided, the filter is contacted with a carbonyl compound, the filter is dried, and the dried filter is contacted with a metal salt solution or metal carboxylate salt solution and an amine-containing compound solution so as to deposit the metal on the surface and within a plurality of the pores. In one embodiment, this filter is then washed and dried. The filter can be any of the filters described above.

The carbonyl compound includes, e.g., aldehydes, sugars, and aldehyde functionality generating compounds. Aldehydes include compounds with the formula $R(CHO)_n$, where R is any aliphatic, aromatic or heteroaromatic group and n is an integer greater or equal to 1. Examples of water soluble aldehydes are glutaraldehyde, formaldehyde, acetaldehyde, butyraldehyde, glyceraldehyde, glyoxal, glyoxal disodium bisulfite, paraldehyde and cyclic trioxanes. Examples of water insoluble aldehydes are cinnamaldehyde and benzaldehyde. By sugar is meant a reducing sugar. Sugars include, e.g., fructose, glucose, lactose, maltose and galactose. By an aldehyde functionality generating compound it is meant a compound capable of generating aldehyde group(s). Examples of such compounds include acetals and hemiacetals. Polymeric acetals, e.g., paraformaldehyde and polyacetal, can also be used in this invention. The carbonyl compound acts as a reducing agent, so that the metal ion is reduced to the metal, e.g., silver ion is reduced to metallic silver. This electroless redox reaction occurs in situ in solution or in the solid state. The carbonyl compound has affinity for aqueous and non-aqueous phases and therefore can be used in the process of coating either hydrophilic or hydrophobic filters. If hydrophobic filters are used, the resulting metal coating confers hydrophilic properties on the coated filter.

After treatment with the carbonyl compound, the filter is either immersed directly into the metal salt solution or metal carboxylate salt solution, or is dried first and then immersed in this solution. Preferably, the filter is first dried. The drying step increases the metal coating within the pores of the filter and produces a more uniform metal coating thickness on the surface and within the pores of the filter. Coating within the pores enhances the bacteriostatic or bacteriocidal properties of the filters.

Any metal which has bacteriostatic or bacteriocidal properties, as described above, can be used in this invention to coat the filters. In a preferred embodiment, the metal is silver. The silver salts that can be used in the metal coating process are salts that are capable of solubilizing, even to a limited degree, in aqueous media, to produce silver ions. Such salts include, e.g., silver nitrate, silver benzoate, silver tartrate and silver acetate, silver citrate or any silver carboxylate.

Metal carboxylate salts include compounds with the formula $R(COO^-M^+)_n$, where R is any aliphatic, aromatic or heteroaromatic group and n is an integer greater or equal to 1. Examples of metal carboxylate salts include, e.g., silver, zinc, cadmium, mercury, antimony, gold, aluminum, copper, platinum and palladium salts of acetic, propanoic, lactic or benzoic acid; and mono-or di-sodium or potassium salts of diacids, e.g., oxalic, malonic, glutaric or tartaric acids. The term metal carboxylate salts is also meant to include carboxylic acids which are capable of forming carboxylate salts in situ under conditions including the presence of a base and a metal ion, and compounds which are capable of forming carboxylic or carboxylate groups in situ, including, e.g., esters, lactones, anhydrides and amides.

By amine-containing compound it is meant a compound capable of producing a metal-amine complex when metal salts react with amines under basic conditions. Examples of amine-containing compounds include ammonium hydroxide, ammonia, and aliphatic, aromatic and heteroaromatic amines.

In another embodiment, a filter having pores is provided, the filter is contacted with an activator, the filter is dried, and the dried filter is contacted with a metal salt or metal carboxylate salt solution so as to deposit the metal on the surface and within a plurality of the pores of the filter. The activator is a salt of a metal including, e.g., tin, titanium, vanadium, chromium, manganese, iron, cobalt, nickel, copper, zinc, germanium, selenium, zirconium, niobium, molybdenum, technetium, ruthenium, rhodium, palladium, antimony, tellurium and lead. A preferred activator is tin dichloride. An alternative embodiment is to contact the dried filter with an amine containing compound in addition to the metal salt or metal carboxylate salt solution.

Additionally, many types of metals can be electroplated onto the surface of suitably primed polymeric materials using standard well known techniques. It is necessary to prime the polymer surface to allow for the electroplating process to occur because most polymers are electrically insulating and do not carry an electrical current. Priming deposits a very small amount of metal onto the surface of the polymer allowing for the subsequent electrolytic deposition of a metal from solution.

The metal coating on the filters derived from any of the methods discussed above, can be further treated to produce a metal oxide coating, as described in Example 7.

This invention also includes the products made in accordance with these methods.

This invention also provides a method for dispensing sterile liquid by applying pressure to the container of the liquid dispenser of this invention so as to discharge the sterile liquid from the container. In one embodiment, the container has an elastically deformable wall, pressure is applied to deform the wall and force the sterile liquid from the container through the filter, and the wall is allowed to recover so as to draw gas from the surrounding atmosphere into the container, the gas being sterilized as it passes through the filter.

The liquid dispenser can be used for any purpose which requires dispensing a sterile solution from a container. Such uses include, e.g., medical related purposes, e.g., dispensing sterile liquids onto any part of the body of an organism or onto an object that is to be placed into the body of an organism, e.g, for use in eye, ear, or nose care. For example, this invention provides a method for using the liquid dispenser of this invention for eyecare in an organism in which a sterile eyecare liquid is dispensed into an eye of the organism or onto an object that is to be placed into the eye of the organism. Preferably, the sterile eyecare liquid is preservative-free. The sterile eyecare liquid includes, e.g., liquid artificial tears, a solution for contact lens care or a medicament. Examples of medicaments are antibiotics, decongestants, anti-inflammatories, anti-glaucoma agents, anti-bacterial agents, anti-viral agents, anesthetics, mydriatics, anti-cholingerics and miotics. An object that is to be placed into the eye includes, e.g., a contact lens. Other uses include process filters for sterilization of all types of solutions, e.g., drug solutions and instillation solutions; intravenous catheters, where a membrane unit is employed for the admittance of air but prevents back flow of blood or other liquids; process filters for food products where sterility is required; dispensation of items such as baby formula where the presence of a preservative would be undesirable; and membrane filter units, e.g., for campers and hikers where the generation of microbial free water is desired without the possibility of future contamination.

EXAMPLES

Example 1

Metal Vapor Deposition (MVD) of Silver Onto a Polyethersulfone Membrane

This example illustrates a method for depositing silver onto a surface, but not within the pores, of a membrane filter. A precut polyethersulfone membrane (Supor 400, pore size 0.45 µM, hydrophilic) (obtained from Gelman of Ann Arbor, Mich.) was mounted on a plate such that the surface to be coated faced the heating source of a metal evaporator. An approximately 4–6 inch long silver wire (obtained from Johnson Matthey of Wardhill, Mass.) was rolled into a coil and placed on the metal bridge in the evaporator. The evaporator was pumped down to $10^{-5}$ Torr and a current of approximately 60–70 amperes was applied to melt the silver. A uniform silver coating of the membrane surface resulted in about 15–30 secs. The current was turned off and the evaporator chamber was allowed to return to atmospheric pressure. The membrane was turned over and the procedure repeated. The resulting membrane had a uniform coating of silver on both surfaces, but not within the pores, as determined by scanning electron microscopy (SEM) and energy dispersive X-ray analysis (EDX).

Example 2

Electroless Coating of Silver Onto a Polyethersulfone Membrane (Method 1)

This example illustrates a method for depositing metallic silver onto a surface, and within the pores, of a membrane filter. A polyethersulfone membrane (Supor 400, pore size 0.45 µM, hydrophilic) (Gelman) was precut into a 47 mm disk. This membrane was immersed in 5 ml of glutaraldehyde (25% solution) (obtained from Aldrich of Milwaukee, Wis.) for 1 min. at 22° C., removed from the aldehyde solution and air dried thoroughly. The treated membrane was then immersed in 5 ml of the silver coating solution described in Example 6A, at pH approximately 12 (the pH can range from approximately 8–14), at 35° C. for 15 secs. The plated membrane was thoroughly rinsed with distilled water and dried in a vacuum oven at 20° C. for 2 hrs. SEM coupled with EDX showed uniform silver coating on the membrane surface and within the pores.

Example 3

Electroless Coating of Silver Onto a Polyethersulfone Membrane (Method 2)

This example illustrates a method for depositing metallic silver onto a surface and within the pores of a membrane filter. A polyethersulfone membrane (Millipore, pore size 0.45 µM, hydrophobic) (obtained from Millipore Corp. of Bedford, Mass.), was precut into a 47 mm disk. This membrane was immersed in 5 ml of 0.1M α-D-glucose in an aqueous solution containing 10% ethanol for 5 mins at 22° C., removed from the sugar solution and air dried throughly. The treated membrane was then immersed in 5 ml of the silver coating solution described in Example 6A, at pH approximately 12 at 35° C. for 2 mins. The plated membrane was thoroughly rinsed with distilled water and dried in a vacuum oven at 20° C. for 2 hrs. SEM coupled with EDX showed uniform silver coating on the membrane surface and within the pores.

Example 4

Electroless Coating of Silver Onto a Polyethersulfone Membrane (Method 3)

This example illustrates a method for depositing metallic silver onto a surface and within the pores of a membrane filter. A polyethersulfone membrane (Gelman Supor 400, pore size 0.45 µM, hydrophilic) was precut into a 47 mm disk. This membrane was immersed in 5 ml of the silver coating solution described in Example 6B, which was heated to 55° C. and maintained at this temperature for 5 mins. The plated membrane was thoroughly rinsed with distilled water and dried in a vacuum oven at 20° C. for 2 hrs. SEM coupled with EDX showed uniform silver coating on the membrane surface and within the pores.

Example 5

Electroless Coating of Silver Onto a Polyethersulfone Membrane: (Method 4)

This example illustrates a method for depositing metallic silver onto a surface and within the pores of a membrane filter. A polyethersulfone membrane (Gelman Supor 400, pore size 0.45 µM, hydrophilic) was precut into a 47 mm disk. This membrane was immersed in 5 ml of a solution containing 1 g tin dichloride, 1 ml concentrated HCl and 9 ml distilled water, at room temperature for 5 mins. The membrane was dried and immersed in the silver coating solution, described in Example 6B, which was then heated to 55° C. and maintained at this temperature for 3 mins. A rapid deposition of metallic silver on the membrane surface ensued. The plated membrane was thoroughly rinsed with distilled water and dried in a vacuum oven at 20° C. SEM coupled with EDX showed uniform silver coating on the membrane surface and within the pores.

Salts of other metals including titanium, vanadium, chromium, manganese, iron, cobalt, nickel, copper, zinc, germanium, selenium, zirconium, niobium, molybdenum, technetium, ruthenium, rhodium, palladium, antimony, tellurium and lead may be used as activators in place of tin dichloride prior to silver plating.

Example 6

Preparation of Silver Coating Solutions (A) This example illustrates the preparation of the silver coating solution that is used in Examples 2, 3 and 10. 3 ml of a silver nitrate solution (10 g silver nitrate dissolved in 10 ml distilled water) was added to 3 ml of a sodium hydroxide solution (10 g sodium hydroxide dissolved in 10 ml distilled water) at 22° C. A brown precipitate of silver oxide formed rapidly. Concentrated ammonium hydroxide (28% ammonia, obtained from EM Science of Gibbstown, N.J.) was added dropwise to the solution until the silver oxide dissolved completely to give a clear solution of a soluble silver amine complex with a pH of 12.

(B) This example illustrates the preparation of the silver coating solution that is used in Examples 4 and 5. 3 ml of a sodium tartrate solution (1 g tartaric acid disodium salt dihydrate (obtained from Aldrich) dissolved in 20 ml distilled water) was added to 3 ml of a silver nitrate solution (10 g silver nitrate dissolved in 10 ml distilled water) at 22° C. A white precipitate of silver tartrate formed rapidly. Concentrated ammonium hydroxide, 28% ammonia (obtained from EM Science), was added dropwise to the solution until the silver tartrate dissolved completely to give a clear solution of ammonical silver tartarate with a pH of approximately 12.

Example 7

Oxygen Plasma Treatment of Silver Coated Membrane Filters

This example illustrates a method for treating a silver coated membrane filter with oxygen plasma so as to produce a silver oxide coating. A silver coated polyethersulfone membrane, obtained from either Example 1 or 2, was mounted on a glass holder and placed inside the reaction chamber of a plasma reactor so that both surfaces of the filter were exposed to the plasma. The reaction chamber was purged with oxygen three times. The pressure of the chamber was adjusted to 300 mTorr, the power maintained at 100 watts, and the membrane subjected to oxygen plasma for 2 mins.

Example 8

Surface Modification of Silver Coated Membrane Filters

This example illustrates a method for treating a silver coated membrane filter with a second compound that has anti-bacterial or anti-viral properties. 3.44 mg (20 mmol) of benzalkoniumchloride thiol (BAC-S), obtained as described in Example 9, was dissolved in 5 ml of absolute ethanol that was degassed for 1 hr under dry nitrogen. A freshly silver coated polyethersulfone membrane obtained from Example 1 or 2, was immersed in this solution at 22° C. for 16 hrs, rinsed in absolute ethanol, and dried under a stream of nitrogen.

Example 9

Synthesis of Benzalkoniumchloride Thiol (BAC-S)

This example illustrates a method for the synthesis of BAC-S from 10-chlorodecanethiol which in turn is synthesized from ω-chlorodecanethioacetate.

(a) ω-Chlorodecanethioacetate

Triphenylphosphine (6.53 g, 25 mmol) (obtained from Aldrich) was dissolved in 95 ml of dry, distilled tetrahydrofuran and the solution was cooled to 0° C. under dry nitrogen. 4.9 ml (25 mmol) of di-isopropylazodicarbonate (obtained from Aldrich) was added to the solution. The reaction mixture was stirred for 30 min. at 0° C. during which time a white precipitate formed. A 1M solution of 10-chloro-1-decanol (4.82 g in 25 ml THF (tetrahydrofuran) (obtained from VWR Scientific of Boston, Mass.) was added. 2.3 g of thiolacetic acid (obtained from Aldrich) in 20 ml THF was subsequently added. The resulting clear solution was stirred at 0° C. for 15 mins and warmed to room temperature. Two drops of water were added. The solvent was removed under reduced pressure, the residue was dissolved with ethyl ether and crystals of triphenylphosphine oxide were removed by filtration. Evaporation of the ether resulted in the crude product, ω-chlorodecanethioacetate, as a yellow oil. This product was distilled under reduced pressure (92°–95° C./10 mM) to give the pure compound as a pale yellow oil (3.23 g, 57%). IR neat, KBr plates cM–1: 1728,s, (O=C—S), TLC, silica (hexane:dichloromethane, 60:40 eluent) Rf=0.7.

(b) 10-Chlorodecanethiol

ω-Chlorodecanethioacetate (3.2 g, 1.2 mmol) was hydrolyzed in 30 ml of methanol, that was degassed under dry nitrogen for 4 hrs, containing 1.6 g (1.2 mmol) anhydrous potassium carbonate (obtained from Aldrich) at 22° C. The suspension was stirred for 1 hr, and then quenched with 0.75 ml glacial acetic acid (obtained from VWR Scientific). The potassium carbonate was filtered and the solvent removed under reduced pressure to yield 10-chlorodecanethiol as a pale yellow oil, 2.4 g, 1.1 mmol). TLC, silica (hexane:dichloromethane, 60:40 eluent) Rf=0.

(c) Benzalkoniumchloride Thiol (BAC-S)

2.4 g (11 mmol) of 10-chlorodecanethiol was reacted with 1.8 g (14 mmol) of N,N-dimethylbenzylamine (obtained from Aldrich) in 50 ml of dry THF. The reaction mixture was refluxed for 20 hrs and cooled. White crystals of BAC-S separated out. These crystals were filtered, washed with THF and dried, yielding 0.85 g of product.

Example 10

Electroless Coating of Silver Onto Tubing For Use in Nozzle Assembly

This example illustrates a method for depositing silver onto the inner surface of tubing which can be used for the passageway walls in the nozzle assembly of the liquid dispenser. Polyethylene tubing (2 inches long, 800 μM ID) (obtained from Putnam Plastics Corp. of Dayville, Conn.) was immersed in a 25% aq. glutaraldehyde solution and ultrasonicated at 20° C. for 2 mins. The tubing was then dried thoroughly and silver coating solution, as described in Example 6A, was drawn into the tubing with a pipette. The plating solution was allowed to soak inside the tubing for 3 mins at 20° C., the excess solution was then expelled and the inside of the tubing was flushed with distilled water. A uniform silver coating resulted on the inside surface of the tubing.

The tubing was tested for bacteriocidal activity. Control or silver treated plastic tubing was inoculated with 10 μls of a suspension of *Pseudomonas dimunata* containing $5 \times 10^7$ organisms. The tubes containing bacterial suspension were incubated 15 hours at 37° C., at which time the tubes were placed in thioglycollate bacterial culture medium (1 cc) and vortexed. Aliquots of this solution were removed and serially diluted and 100 μls of these dilutions were plated onto NZY agar plates. The plates were incubated overnight at 37° C. and the bacterial concentrations were determined by counting bacterial colonies.

Example 11

Surface Modification of Silver Plated Membrane to Give Hydrophobic/Hydrophilic Surface This example illustrates a method for producing a silver coated membrane filter that is partially hydrophobic and partially hydrophilic. 20.2 mg (20 mmol) of 1-dodecanethiol (obtained from Sigma Chemical Co., St. Louis, Mo.) was dissolved in 5 ml of absolute ethanol that was degassed for 1 hr under dry nitrogen. A freshly silver coated (by MVD or electroless process) polyethersulfone membrane (Gelman Supor 400, pore size 0.45 μM, hydrophilic) was partially immersed in this solution at 22° C. for 16 hours. The membrane was then rinsed in absolute ethanol and dried under a stream of nitrogen. The resulting surface treated membrane was hydrophobic (non-wetting) in the area treated with the alkyl thiol while remaining hydrophilic in the non-treated area.

Example 12

Silver Coating of Polymethylmethacrylate (PMMA) Sheets

This example illustrates a method for depositing metallic silver onto the surface of PMMA sheets. A commercially obtained PMMA sheet was cut in the form of a slide and the surface was cleaned by ultrasonication in absolute ethanol for 1 minute at room temperature. The cleaned slide was then immersed in 30 ml of an activator solution consisting of 10% tin dichloride dihydrate ($SnCl_2 2H_2O$) (obtained from Allied Chemicals of New York, N.Y.), 45% absolute ethanol and 45% distilled water and ultrasonicated at 45° C. for 15 minutes. The slide was then rinsed several times with distilled water. It was then immersed in a 10% aqueous solution of silver nitrate for 15 minutes at room temperature. During this time the slide acquired a brown tinge due to the deposition of silver. The coated slide was then rinsed with distilled water and dried. The silver coating was adherent to the polymer and did not cause loss of transparency of the slide.

Example 13

Silver Coating of Polypropylene (PP)

This example illustrates a method for depositing a metallic silver coating onto the surface of polypropylene slides (obtained from Eastman Chemical Product, Inc., Kingsport, Tenn.). The slides were immersed in 30 ml of a 5% solution of chlorosulfonic acid (obtained from Aldrich of Milwaukee, Wis.) in chloroform at 50° C. for 5 mins. They were allowed to dry for 15 mins. then immersed in a 1M aqueous solution of sodium hydroxide after which they were rinsed thoroughly with distilled water. The surface treated slides were subjected to the silver coating procedure described in Example 4 using the plating solution described in Example 6B. This resulted in a uniform silver coating that is adherent to the polypropylene surface.

Example 14

Anti-bacterial Properties of Differently Treated Membrane Filters

This example illustrates a method for testing different types of membrane filters with different pore sizes, which have been coated with different compounds by different procedures, for their bacteriocidal/bacteriostatic properties.

Filters, either control or treated, were placed into Gelman plastic filter holders and the entire unit was autoclaved 30 minutes at 121° C. Using aseptic techniques under a laminar flow hood, sterile bacterial media, sterile saline solution or a preservative free artificial tear solution ("Hypo Tears," obtained from Johnson and Johnson) was introduced to eliminate air pockets and to ensure proper flow through the assembled filter apparatus. The challenge organism, either *Pseudomonas dimunata*, or a cocktail of *Pseudomonas dimunata, Bacillus subtilis, Bacillus vulgaris* and *Escherichia coli*, at a concentration of $10^7$ organisms per ml, was purged through the filter using a 3 cc syringe and manual pressure. Approximately 1 cc of liquid was expelled first and was checked for sterility so to ensure that the membrane was properly sealed. Three drops of eluate were collected and tested for sterility. The outlet tip was maintained in a sterile environment using a clean sterile cover and the entire unit was stored at 37° C. for the course of the experiment. The sterility of the eluate was tested daily by collecting three drops (approximately 150 μl) of bacteria/media inoculum into sterile thioglycollate medium which was then placed in a 37° C. shaker overnight and assessed the next day for sterility. As the medium/bacteria inoculum level lowered over the course of the experiment, the input syringe was removed and fresh sterile media was added and reattached to the filter holder unit. A filter was considered to have "failed" when the sterility check failed on two consecutive tests, the failed filter apparatus still held air pressure under water, and the failed sterility check demonstrated by gram stain the expected morphology of the test organism.

Table 1 summarizes the results. "GS" is Gelman Supor 400 membranes; "GH" is Gelman HT650 membranes; "M" is Millipore membranes. The type of material that the membranes are composed of is indicated by "PES" for polyethersulfone and "PVDF" for polyvinylidene fluoride. "μM" indicates the micron pore size of the membrane. "–" indicates that the membrane was untreated. "MVDAg" indicates the membrane was treated to produce a silver coating by the metal vapor deposition method as described in Example 1. "TAg" indicates the membrane was treated to produce a silver coating by the electroless method of this invention as described in Example 2, Method 1. "+P" indicates the silver coated membrane was treated with oxygen plasma to produce a silver oxide coating as described Example 7. "+B" indicates that the silver coated membrane was treated with BAC-S (benzalkoniumchloride thiol) to produce a layer of BAC-S over the silver coating as described in Example 8.

The numbers in the "Days" column indicate the average number of days until the filter failed, as determined by the criteria discussed above. A ">#" indicates that no failure was detected for the duration of the test, i.e., the number of days indicated.

The various growth media used are indicated by "B" for sterile bacterial media, "S" for sterile saline solution, and "T" for "Hypo Tears," a preservative free artificial tear solution by Johnson & Johnson. Sterilization of the membranes was achieved either by autoclaving at 121° C. for 30 minutes ("A"), or placement in absolute ethanol for 20 minutes ("Et"). The "No." indicates the number of samples of membranes that were tested.

TABLE 1

Bacterial Challenge Experiments on Silver Coated Membranes

| Mfgr | Type | mM | Treatment | Days | Growth Medium | Sterilization | No. |
|---|---|---|---|---|---|---|---|
| GS | PES | 0.45 | — | 7 | B | A | 3 |
| GS | PES | 0.45 | MVDAg + P | 10 | B | A | 3 |
| GS | PES | 0.45 | TAg | 22 | B | A | 3 |
| GS | PES | 0.45 | TAg + P | 16 | B | A | 3 |
| GS | PES | 0.45 | MVDAg + B | 14 | B | A | 3 |
| GS | PES | 0.45 | TAg + B | >77 | B | A | 3 |
| GS | PES | 0.45 | — | 7 | B | A | 9 |
| GS | PES | 0.45 | TAg | >25 | B | A | 6 |
| GS | PES | 0.45 | — | 10 | T | A | 9 |
| GS | PES | 0.45 | TAg | >76 | T | A | 9 |
| GS | PES | 0.45 | — | 3 | S | A | 6 |
| GS | PES | 0.45 | TAg | >43 | S | A | 6 |
| GH | PES | 0.65 | — | 4 | T | A | 3 |
| GH | PES | 0.65 | TAg | >88 | T | A | 3 |
| GS | PES | 0.65 | — | 1 | S | A | 5 |
| GS | PES | 0.65 | TAg | >43 | S | A | 5 |
| M | PVDF | 0.22 | — | 5 | B | Et | 1 |
| M | PVDF | 0.22 | MVDAg | >14 | B | Et | 1 |
| M | PVDF | 0.22 | MVDAg + P | >14 | B | Et | 1 |
| M | PVDF | 0.22 | TAg | >14 | B | Et | 1 |
| M | PVDF | 0.22 | TAg + P | >14 | B | Et | 1 |
| M | PVDF | 0.22 | TAg + B | >14 | B | Et | 1 |
| M | PVDF | 0.22 | — | 15 | B | A | 3 |
| M | PVDF | 0.22 | TAg | >70 | B | A | 3 |
| M | PVDF | 0,45 | — | 2 | B | Et | 1 |
| M | PVDF | 0.45 | MVDAg | 5 | B | Et | 1 |
| M | PVDF | 0.45 | MVDAg + P | >11 | B | Et | 1 |
| M | PVDF | 0.45 | TAg | >11 | B | Et | 1 |
| M | PVDF | 0.45 | — | 7 | B | A | 3 |
| M | PVDF | 0.45 | TAg | >70 | B | A | 3 |

Those skilled in the art will be able to ascertain, using no more than routine experimentation, many equivalents of the specific embodiments of the invention described herein. These and all other equivalents are intended to be encompassed by the following claims.

What is claimed is:

1. A liquid dispenser for dispensing a sterile liquid, comprising:
   a container for storing the sterile liquid;
   a nozzle assembly mounted on said container, said nozzle assembly having a passageway for enabling flow of the sterile liquid therethrough from said container during liquid dispensing; and
   a filter having a downstream and an upstream surface and being attached to said nozzle assembly so that said filter extends across said passageway to direct liquid and air flow through said filter from said container to said downstream surface of said filter;
   said filter being at least partially coated on the downstream surface with a first bacteriostatic or bacteriocidal metallic material consisting essentially of silver, silver oxide, a silver salt, or mixtures thereof;
   said filter having pores with a pore size so as to preclude passage of microorganisms therethrough and so as to permit passage of the sterile liquid from said container therethrough; and
   said filter being at least partially coated within a plurality of said pores with said first metallic material.

2. The liquid dispenser of claim 1 wherein said filter further is at least partially coated on the upstream surface with said first metallic material.

3. The liquid dispenser of claim 1 wherein said downstream surface of said filter and a plurality of said pores are at least partially coated with a second bacteriostatic or bacteriocidal metallic material.

4. The liquid dispenser of claim 3 wherein said filter further is at least partially coated on the upstream surface with said second metallic material.

5. The liquid dispenser of claim 1 wherein said filter is selected from the group consisting of organic and inorganic filters and said container is formed of an elastically deformable polymer.

6. The liquid dispenser of claim 1 wherein said pore size is in the range of approximately 0.1 microns to approximately 1.2 microns.

7. The liquid dispenser of claim 1 wherein said pore size is in the range of approximately 0.22 microns to approximately 0.65 microns.

8. The liquid dispenser of claim 1 wherein said filter includes a hydrophobic portion for allowing air to enter said container to replace the sterile liquid dispensed therefrom.

9. The liquid dispenser of claim 1 wherein said nozzle assembly has internal walls surrounding said passageway, and said walls are at least partially coated with a metallic material selected from the group consisting of silver, a silver oxide, a silver salt, and mixtures thereof.

10. The liquid dispenser of claim 1 further comprising a prefilter being spaced upstream from said filter for providing a barrier to the passage of particulate matter therethrough and for permitting the passage of sterile liquid from said container therethrough.

11. The liquid dispenser of claim 1 further comprising a support being spaced upstream from said filter for reinforcement of said filter.

12. The liquid dispenser of claim 1 comprising a multi-dose dispenser.

13. The liquid dispenser of claim 1 wherein said downstream surface of said filter and a plurality of said pores further comprises at least a partial additional coating with a nonmetallic compound that has an anti-viral or anti-bacterial property.

14. A method of dispensing a sterile liquid comprising applying pressure to the container of the liquid dispenser of claim 1 so as to discharge the sterile liquid through said filter from said container.

15. The method of claim 14 wherein said container comprises an elastically deformable wall portion,
   said pressure being applied to deform said wall portion and force the sterile liquid from said container through said filter, and
   allowing rebound of said wall portion to draw gas from a surrounding atmosphere into said container while said gas is sterilized by said filter in passing therethrough.

16. A method of using a liquid dispenser of claim 1 for eyecare in an organism comprising dispensing a sterile eyecare liquid from said liquid dispenser into an eye of said organism or onto an object that is to be placed into the eye of said organism.

17. The method of claim 16 wherein said sterile eyecare liquid is selected from the group consisting of liquid artificial tears, a solution for contact lens care and a medicament.

18. A dispenser for dispensing sterile liquids, said dispenser having a filter attached to a container for said liquids, the improvement comprising:

said filter being at least partially coated on a downstream surface thereof with a metallic material consisting essentially of a silver, a silver oxide, a silver salt, or mixtures thereof;

said filter extending across a passageway provided by said container leading from said container to a dispensing area where said liquid is dispensed;

said filter having pores with a pore size so as to preclude passage of microorganisms therethrough and so as to permit passage of the sterile liquid from said container therethrough; and said filter being at least partially coated within a plurality of said pores with said metallic material.

* * * * *